United States Patent [19]

Crivello et al.

[11] Patent Number: 5,260,399
[45] Date of Patent: Nov. 9, 1993

[54] REGIOSPECIFIC CATALYST FOR THE SYNTHESIS OF EPOXYSILOXANE MONOMERS AND POLYMERS

[75] Inventors: James V. Crivello, Clifton Park; Mingxin Fan, Troy, both of N.Y.

[73] Assignee: General Electric Company, Waterford, N.Y.

[21] Appl. No.: 895,315

[22] Filed: Jun. 8, 1992

[51] Int. Cl.$^5$ ............................................. C08G 77/06
[52] U.S. Cl. ........................................ 528/15; 528/14; 528/23; 525/474; 525/476
[58] Field of Search .............................. 528/15, 14, 23; 525/474, 476

[56] References Cited

U.S. PATENT DOCUMENTS 4,617,238 10/1986 Crivello et al. ..................... 428/452

Primary Examiner—Melvyn I. Marquis

[57] ABSTRACT

The invention provides a method for making an epoxysilicone compound through the hydrosilation addition reaction between an ethylenically unsaturated epoxide and an SiH-containing silicon to produce an epoxysilicone product, and catalyzed by a regiospecific hydrosilation catalyst which does not also promote an oxirane ring-opening polymerization reaction in either the ethylenically unsaturated epoxide starting compound or in the epoxysilicone hydrosilation reaction product. The invention also provides a hydrosilation catalyst with the above catalytic properties as well as an epoxysilicone composition made by the above method.

15 Claims, No Drawings

REGIOSPECIFIC CATALYST FOR THE SYNTHESIS OF EPOXYSILOXANE MONOMERS AND POLYMERS

The present invention relates to a method of producing epoxysilicones using a catalyst that efficiently promotes the hydrosilation addition reaction between an ethylenically unsaturated epoxide and a SiH-containing silane or siloxane, but which does not also promote epoxide oxirane ring-opening polymerization of the ethylenically unsaturated epoxide starting material or the epoxysilicone monomer or polymer product. The invention also relates to catalysts with the above-stated properties as well as to a curable epoxysilicone composition made by the above method.

BACKGROUND OF THE INVENTION

In the production of epoxysilicone compositions, transition metal catalysts have long been known to promote the hydrosilation reaction. See, for example, J. L. Speier, "Homogeneous Catalysis of Hydrosilation by Transition Metals", in *Advances in Organometallic Chemistry*, Vol. 17, pp. 407–447 (1979), F. G. A. Stone and R. West, eds., Academic Press (New York, San Francisco, London); Aylett, *Organometallic Compounds*, Vol. 1, John Wiley, New York 1979, p. 107; and Crivello and Lee, "The Synthesis, Characterization, and Photoinitiated Cationic Polymerization of Silicon-Containing Epoxy Resins", *J. Polymer Sci.*, Vol. 28, John Wiley, New York 1990, pp. 479–503. Generally, the hydrosilation catalysts used are complexes of platinum, palladium, rhodium, iridium, iron or cobalt. In particular, platinum-containing catalysts have been widely used for this purpose.

However, it has been found that in addition to catalyzing the hydrosilation reaction between an ethylenically unsaturated epoxide and a silicon hydride, in the presence of silicon hydrides many transition-metal-complex hydrosilation catalysts also promote the oxirane ring-opening polymerization of the ethylenically unsaturated epoxide starting material and the epoxysilicone product of the hydrosilation reaction. Copending, commonly assigned Application serial no. 07/473,802 (Riding, et al.), filed February 2, 1990, discloses the use of platinum or platinum-based catalysts to promote the oxirane ring-opening polymerization of epoxides. This ring-opening polymerization reaction during production of an epoxysilicone is undesirable as the epoxide polymerization may cause the reaction mixture to gel completely, resulting in the loss of the entire batch and in loss of considerable time in cleanup of the insoluble gelled resin.

Additionally, a partial gelation due to the ring-opening polymerization reaction can occur during synthesis such that reproducible batch-to-batch viscosity of the epoxysilicone product is difficult to obtain. Such reproducibility in viscosity is highly preferred in the epoxysilicone industry, as these materials are typically used as coatings, for example release coatings, and the process of successfully and uniformly applying these coatings to a substrate is highly dependent upon the viscosity of the coating material. Commonly assigned, co-pending applications to Eckberg, et al., U.S. patent application Ser. No. 802,679, filed Dec. 5, 1991, U.S. patent application Ser. Nos. 5,227,410 and 802,681, filed Dec. 5, 1991, disclose that viscosity control can be achieved by use of a tertiary amine stabilizer during the hydrosilation synthesis reaction. However, only certain catalysts are active in the presence of this stabilizer.

Furthermore, in the presence of precious metal hydrosilation catalysts, epoxysilicones have been found to slowly gel on storage at room temperature due to the epoxide ring-opening polymerization reaction, thus shortening the shelf-life of the epoxysilicone product. While this storage problem can be partially alleviated by deactivating the transition-metal-complex catalyst with an inhibitor of its catalytic activity, such as dodecyl mercaptan or 2-mercaptobenzothiazole in the case of platinum complexes, it would be preferable to not incorporate this extra component and additional process step into epoxysilicone composition and production process.

In order to minimize the oxirane ring-opening polymerization reaction, epoxysilicone fluids have been previously successfully produced only by careful control of batch temperature and olefin epoxide feed rate during the synthesis, followed by the above-mentioned inactivation of the catalyst after the completion of the hydrosilation reaction.

Certain hydrosilation catalysts containing phosphine ligands are known. For example, as disclosed by de Charentenay, F., Osborn, J. A., and Wilkinson, G., *J. Chem. Soc. A.* 1968, p.787, $RhCl[(C_6H_5)_3P]_3$ (Wilkinson's catalyst) efficiently catalyzes the hydrosilation reaction between SiH-containing silanes and siloxanes and vinyl epoxides. However, it was not previously known whether $RhCl[(C_6H_5)_3P]_3$ or other phosphine-containing catalysts also catalyze the epoxide ring-opening reaction described above.

As disclosed in commonly assigned U.S. patent application of Crivello and Fan, entitled "Preparation of Epoxysilicon Compounds using Rhodium Catalysts", U.S. Pat. No. 5,169,962 issued on Dec. 8, 1962 rhodium-based hydrosilation catalysts selectively promote the hydrosilation reaction without the promotion of an epoxide ring-opening polymerization reaction. A variety of epoxy-containing silicone monomers and oligomers can be synthesized using these catalysts. However, most of the catalysts traditionally used for synthesis of epoxysilicone compositions, particularly Pt-containing catalysts, do promote the epoxide ring-opening polymerization reaction, and therefore do not permit the selective hydrosilation synthesis of epoxysilicones.

There, therefore, exists a need in the epoxysilicone industry for a method of eliminating the oxirane ring-opening when employing commonly used hydrosilation catalysts. There also exists a need for an efficient yet economical method of producing epoxysilicone monomers and oligomers in the absence of the epoxide ring-opening side reaction, thereby producing epoxysilicone compositions of reproducible viscosity. There is additionally a need for epoxysilicone composition which is stable to the epoxide ring-opening reaction and, therefore, has an increased shelf-life without the additional step and cost of poisoning the catalyst after the completion of the hydrosilation addition reaction.

It is, thus, an object of the present invention to provide a method for preparing an epoxysilicone composition through the reaction between an ethylenically unsaturated epoxide and an organohydrogensilane or organohydrogensiloxane in the presence of a catalyst which efficiently promotes the hydrosilation reaction without also promoting the afore-mentioned oxirane ring-opening polymerization of either the ethylenically unsaturated epoxide starting material or the epoxysilicone product.

It is another object of the invention to provide a hydrosilation catalyst for the addition reaction between an olefin epoxide and a SiH-containing silane or siloxane to form an epoxysilicone compound, wherein the catalyst effectively promotes the hydrosilation reaction without also promoting the ring-opening polymerization of the epoxide ring in either the olefin epoxide starting material or the epoxysilicone product.

Still another object of the invention is to provide an epoxysilicone composition with reproducible batch-to-batch viscosity and enhanced storage life, and which is stable to oxirane ring-opening polymerization at room temperature.

SUMMARY OF THE INVENTION

The present invention provides a method for making an epoxy-containing organosilicon compound, comprising the steps of:

i) preparing a mixture comprising:

(A) 1 part by weight of an ethylenically unsaturated epoxide;

(B) from about 0.5 to about 400 parts by weight of an organohydrogensiloxane or an organohydrogensilane, as compared to the weight of (A); and (C) from about 1 to about 5000 parts per million by weight as compared to the weight of (A) a hydrosilation catalyst comprising a phosphine ligand and a non-phosphine-containing transition-metal complex; and wherein the weight ratio of said phosphine ligand to said non-phosphine-containing transition metal complex in said mixture is from about 1:10 to about 250:1.

(ii) reacting the mixture of said step (i), at a temperature of from about 25° C. to about 120° C. under conditions which promote a hydrosilation addition reaction between an olefin epoxide and a silicon hydride to produce an epoxysilicone product, and which do not promote an epoxide ring-opening reaction in either (A) or in said epoxysilicone product.

The invention also provides a curable composition comprising Components (A), (B) and (C) used in the method described above. The curable composition of the invention has the desirable qualities of batch-to-batch reproducibility in viscosity and enhanced storage life at room temperature.

The invention further provides a phosphine-containing or phosphine-modified transition-metal-complex hydrosilation catalyst for the production of epoxysilicone monomers and oligomers, wherein the catalyst effectively promotes the hydrosilation reaction between an ethylenically unsaturated epoxide and an organohydrogensilane or organohydrogensiloxane, without also promoting an oxirane ring-opening polymerization reaction in either the ethylenically unsaturated epoxide starting material or in the epoxysilicone product.

DETAILED DESCRIPTION OF THE INVENTION

The present invention is based on the unexpected discovery that transition-metal complexes employing phosphine ligands or, alternatively, in the presence of phosphine ligands are effective for promoting the addition of ethylenically unsaturated epoxides to silicon hydrides without also promoting the oxirane ring-opening polymerization reaction of the epoxide starting material or the epoxysilicone final product.

The present invention provides a method for making an epoxy-containing organosilicon compound, comprising the steps of:

(i) preparing a mixture comprising:

(A) 1 part by weight of an ethylenically unsaturated epoxide;

(B) from about 0.5 to about 400 parts by weight of an organohydrogensiloxane or an organohydrogensilane, as compared to the weight of (A); and (C) from about 1 to about 5000 parts per million by weight as compared to the weight of (A) a hydrosilation catalyst comprising a phosphine ligand and a non-phosphine-containing transition-metal complex; and wherein the weight ratio of said phosphine ligand to said non-phosphine-containing transition metal complex in said mixture is from about 1:10 to about 250:1.

(ii) reacting the mixture of said step (i), at a temperature of from about 25° C. to about 120° C. under conditions which promote a hydrosilation addition reaction between an olefin epoxide and a silicon hydride to produce an epoxysilicone product, and which do not promote an epoxide ring-opening reaction in either (A) or in said epoxysilicone product.

The invention also provides a curable composition comprising Components (A), (B) and (C) used in the method described above.

The invention further provides a phosphine-containing or phosphine-modified transition-metal hydrosilation catalyst for the production of epoxysilicone monomers and oligomers, wherein the catalyst effectively promotes the hydrosilation reaction between an ethylenically unsaturated epoxide and an organohydrogensilane or organohydrogensiloxane, without promoting an oxirane ring-opening polymerization reaction in either the ethylenically unsaturated epoxide starting material or in the epoxysilicone product.

By not promoting the oxirane ring-opening polymerization reaction, the hydrosilation catalyst of the present invention allows the synthesis of highly reactive, curable epoxysilicones with improved viscosity control and without the danger of gelation during or after synthesis, and which are useful in the production of, for example, silicone paper release agents, decorative and protective coatings, inks, adhesives, electronics encapsulants and insulation and other uses of epoxysiloxanes.

Component (A) used in the method and composition of the present invention is an ethylenically unsaturated, i.e., either vinyl- or allyl-functional, epoxide. The ethylenically unsaturated epoxides useful in Component (A) generally include any aliphatic (glycidyl) or cycloaliphatic epoxy compounds having olefinic moieties which will readily undergo the hydrosilation addition reaction to organohydrogensilicon compounds of Component (B). Commercially available examples of such ethylenically unsaturated epoxides useful in the practice of the invention include allyl glycidyl ether; methallyl glycidyl ether; 1-methyl-4-isopropenyl cyclohexene oxide; 2,6-dimethyl-2,3-epoxy-7-octene; 1,4-dimethyl-4-vinylcyclohexene oxide; 4-vinylcyclohexene oxide; vinylnorbornene monoxide; dicyclopentadiene monoxide. Other suitable examples of useful ethylenically unsaturated epoxides include 1,2-epoxy-6-heptene, 1,2-epoxy-3-butene and chemically similar, unsaturated aliphatic, cycloaliphatic, and alkylaromatic epoxides.

The preferred ethylenically unsaturated epoxide is 4-vinylcyclohexene oxide.

Component (B) is an organohydrogensiloxane or organohydrogensilane. Suitable silicon hydrogen-containing starting materials generally include any silicon compound derived from a silane or at least two organosiloxane units having terminal and/or pendant SiH groups. The SiH-containing silicon compounds useful in the practice of the invention are those capable of reacting with the ethylenically unsaturated moieties of the epoxides of Component (A) above via the hydrosilation addition reaction.

Component (B) may be either a linear hydrogen substituted polysiloxane or silane or a cyclic hydrogen substituted polysiloxane or silane, or a combination of the two. The linear hydrogen substituted polysiloxane or silane may be either branched or unbranched.

In addition, Component (B) organohydrogensiloxanes useful in the invention may be copolymers, terpolymers, etc. For example, a polydimethylsiloxane-polymethylhydrogen siloxane copolymer is useful in the practice of the present invention. Additionally, a polyetherorganohydrogensiloxane linear block copolymer, such as those described in copending, commonly assigned U.S. patent application Ser. No. 802,679, of Eckberg, et al., filed Dec. 5, 1991) is useful as Component (B) when UV cure in conjunction with onium salt catalysts is desired in the curable composition of the present invention.

Representative examples of suitable linear SiH-containing compounds include 1,1,3,3-tetraalkyldisiloxane, dialkylhydrogensiloxy-endstopped polydialkylsiloxane, copolymer comprising at least two alkylhydrogensiloxy groups, (e.g., $(CH_3)_2(H)SiO[(CH_3)_2SiO]_x[(CH_3)(H)SiO]_ySi(H)(CH_3)_2$, where x and y are greater than or equal to 1). Other examples of SiH-containing silicon compounds useful in the invention include 1,1,3,3-tetramethyldisiloxane, 2,4,6,8-tetramethylcyclotetrasiloxane, methyldimethoxysilane, triethylsilane, and methyldiethoxysilane. The preferred linear SiH-containing silicon compound for Component (B) in the present invention is 1,1,3,3-tetramethyldisiloxane. The preferable cyclic hydrogen substituted polysiloxane is 2,4,6,8-tetramethylcyclotetrasiloxane.

The preferred Component (B) in the present invention is the aforementioned 1,1,3,3-tetramethyldisiloxane.

Component (B) is used in the method and composition of the present invention in an amount ranging from about 0.5 to about 400, preferably from about 0.5 to about 100, and most preferably from about 0.75 to about 5, parts by weight as compared to the weight of Component (A).

Component (C) of the present invention comprises a transition-metal-complex hydrosilation catalyst, which either contains a phosphine ligand, is modified by premixing with a phosphine ligand prior to addition to Component (A), (B), or both, or is modified by the in situ addition of a phosphine ligand in the hydrosilation reaction mixture. The first of such catalysts is referred to herein as a "phosphine-containing transition-metal complex", whereas the latter two catalysts are referred to as "a phosphine-modified transition-metal complex". The catalysts as described herein have been found to be effective for the selective hydrosilation reaction in the method of the invention, without also promoting an oxirane ring-opening polymerization reaction. Suitable selective hydrosilation catalysts for practicing the invention include phosphine-containing or modified rhodium, iridium, platinum, palladium, nickel, cobalt and ruthenium transition-metal complexes.

The following examples are meant to be illustrative of suitable phosphine-containing, transition-metal complex hydrosilation catalysts useful in the practice of the invention:
$RhX(CO)(PR_3)_2$; $RhH(CO)[(C_6H_5)_3P]_3$; $IrCl(CO)[(C_6H_5)_3P]_2$; $IrI(CO)[(C_6H_5)_3P]_2$; $IrH(CO)[(C_6H_5)_3P]_3$; $Pt[(C_6H_5)_3P]_4$; transPt$[(C_6H_5)_3P]_2Cl_2$; cis-Pt$[(C_6H_5)_3P]_2C_{12}$; $Pt[(C_6H_5)_3P]_2(C_2H_4)$; $Pt[(C_6H_5)_3P]_2O_2$; transPtHCl$[(C_6H_5)_3P]_2$; cis-PtHCl$[(C_6H_5)_3P]_2$; $Pt(PF_3)_4$; $Pd[(C_6H_5)_3P]_2C_{12}$; $Pd[(C_6H_5)_3P]_4$; $Pd[(C_6H_5)_3P]_2(CH_3CO_2)_2$; $Ni[(C_6H_5)_3P]_4$; $Ni[(C_6H_5)_3P]_2Cl_2$; $Co[(C_6H_5)_3P]_2Cl_2$; and $Ru[(C_6H_5)_3P]_3Cl_2$.

In the foregoing examples, X represents a halogen atom, preferably chlorine, and the R substituents may be the same or different in any given complex and may be an alkyl radical having from 1 to 8, inclusive, carbon atoms, or aryl, aralkyl or alkaryl radicals, for example methyl, ethyl, n-butyl, hexyl, phenyl, tolyl, and benzyl. The R groups may be either unsubstituted or substituted. By the term "substituted" it is meant an organic radical having chloro, bromo, iodo, cyano, carboxy, mercapto, hydroxy, thio, amino, nitro, phopho or other groups known in the art. Additionally, heterocyclic and aromatic heterocyclic organic radicals such as pyridyl, thiophenyl, pyranyl, and the like as known in the art are also meant to be encompassed in the definition of "substituted" organic radicals. The R substituents may also represent $R^1_3SiQ$- groups in which Q represents a divalent ali-phatic hydrocarbon radical having from 1 to 6, inclusive, carbon atoms, for example, $-CH_2-$, $-CH_2CH_2-$, and $-CH_2CHCH_3CH_2$-and each $R^1$ represents an alkyl, aryl, aralkyl, or alkaryl radical as defined and exemplified for R, above, or one $R^1$ substituent may represent a trimethylsilyl radical.

The preferred phosphine-containing transition-metal complex hydrosilation catalyst is $Pt[(C_6H_5)_3P]_4$.

In the method, composition and catalyst of the invention, phosphine-containing catalysts are most useful and economical in the range of from about 1 to about 5000 parts per million, preferably from about 1 to about 500, and most preferably from about 10 to about 50 parts per million by weight, based upon the weight of Component (A).

Examples of Component (C) non-phosphine-containing transition-metal complexes that may be either modified in situ by phosphine ligands or mixed with modifying phosphine ligands prior to combining with Components (A) and (B), or both, include:
$RhX_3(SR_2)_3$; $RhX_3 \cdot xH_2O$; [RhX(norbornadiene)]$_2$; [RhCl(cyclooctadiene)]$_2$; [RhCl(C$_2$H$_4$)$_2$]$_2$; [RhCl(CO)$_2$]$_2$; [Rh(CO)$_2$(C$_5$H$_7$O$_2$)]; $Rh_2(CH_3CO_2)_4$; [Rh(C$_7$H$_{15}$O$_2$)$_2$]$_2$; $Rh(C_2H_8N_2)_3Cl_3 \cdot 3H_2O$; $Rh(C_5H_7O_2)_3$;
[IrCl(cyclooctadiene)]$_2$; [IrCl(CO)$_3$]$_n$; Ir(CO)$_2$(C$_5$H$_7$O$_2$)$_2$; cis-[Ir(C$_2$H$_8$N$_2$)$_2$Cl$_2$]Cl; $H_2IrCl_6 \cdot xH_2O$; $IrCl_3 \cdot H_2O$; Pt(pyridine)$_2$Cl$_2$; $H_2PtCl_6 \cdot xH_2O$; (NH$_4$)$_2$PtCl$_6 \cdot xH_2O$; $H_2PtBr_6 \cdot xH_2O$; PtCl$_2$(cyclooctadiene); PtBr$_2$(cyclooctadiene); PtI$_2$(cyclooctadiene); cis-Pt$[(CH_3CH_2)_2S]_2Cl_2$; Pd(pyridine)$_2$Cl$_2$; [PdCl(C$_3$H$_5$)]$_2$; Pd(pyridine)$_2$(CH$_3$CO$_2$)$_2$; PdCl$_2$(cyclooctadiene); PdCl$_2$(C$_6$H$_5$CN)$_2$; Pd(CH$_3$CO$_2$)$_2$; and Co$_2$(CO)$_8$, where X represents a halogen atom, preferably chlorine, x is 3 or 4 and n is an integer from about 2 to about 10. By the term "non-phosphine-containing transition-metal complex" it is meant a transition-metal complex that does not contain as a ligand a phosphine derivative of the formula $PR_{2/3}$, where the $R^2$ groups are individually organic radicals as defined for R above. The preferred non-phosphine-containing transition-metal complex is the aforementioned $PtCl_2$(cyclooctadiene).

In the method, composition and catalyst of the invention, the non-phosphine-containing, transition metal complex is most useful and economical when used in a range of from about 1 to about 5000 parts per million, preferably from about 1 to about 500, and most preferably from about 10 to about 50 parts per million by weight as compared to the weight of Component (A).

In the practice of the invention, the phosphine ligand which modifies the non-phosphine-containing transition metal complexes above may generally be mono, di- or tridentate ligands.

Monodentate phosphine ligands useful in the practice of the invention have the general formula $R_{23}P$, where the $R^2$ groups may be individually alkyl, aryl, alkaryl or aralkyl radicals as defined and exemplified for the R radicals above. Preferred monodentate phosphine ligand include triphenylphosphine, triethylphosphine, tri-n-butylphosphine, trimethylphosphine, diphenylmethylphosphine and dimethylphenylphosphine.

The most preferred monodentate phosphine is the above-mentioned triphenylphosphine.

Examples of preferred didentate and tridentate phosphine ligands useful in the invention include:
$(C_6H_5)_2PCHCHP(C_6H_5)_2$; $(C_6H_5)_2PCH_2CH_2P(C_6H_5)_2$;
$(CH_3CH_2)_2PCH_2CH_2P(CH_2CH_3)_2$;
$(CH_3)_2PCH_2CH_2P(CH_3)2$; $(C_6H_5)_2PCH_2P(C_6H_5)_2$;
and $[(C_6H_5)_2PCH_2CH_2]_2P(C_6H_5)$.

Most preferred multidentate phosphine ligands in the method and composition of the invention are $(C_6H_5)_2PCHCHP(C_6H_5)_2$; $(C_6H_5)_2PCH_2CH_2P(C_6H_5)_2$; and $(CH_3CH_2)_2PCH_2CH_2P(CH_2CH_3)_2$ The amount of modifying phosphine ligand useful in the method, composition and catalyst of the invention will vary depending upon the amount of non-phosphine-containing transition-metal complex employed. In general, about the lowest effective level of ligand used is preferred. This level may be conveniently determined for a specific catalyst concentration through the method for determining whether a given transition-metal complex promotes the epoxide ring-opening polymerization reaction described in the Examples below. For use with the above-stated ranges of non-phosphine-containing catalysts, the phosphine ligands are useful in a weight ratio of phosphine ligand to non-phosphine-containing transition-metal complex from about 1:10 to about 250:1.

In the method, composition and catalyst of the present invention, the non-phosphine-containing transition-metal complex and the modifying phosphine ligand may be either mixed together in the appropriate ratio prior to addition to Components (A) and (B), or the phosphine-modified transition-metal complexes may be generated in the reaction vessel in the presence of either Component (A) or Component (B), or both, simply by simultaneous or sequential addition of these compounds to the vessel. In the case of in situ generation of the phosphine-modified transition-metal complex, there may be a short induction time prior to the initiation of the hydrosilation reaction whereas in the case of pre-mixed Component (C) this induction time is not generally observed.

Additionally, as the non-phosphine-containing transition-metal complex used in the method, composition and catalyst of the invention may itself promote the epoxide ring-opening and hydrosilation addition reactions, it is preferred in the practice of the invention that these compounds and the modifying phosphine ligands be premixed prior to their addition to a batch containing both Components (A) and (B) such that Component (C) is added as a single mixture to the reaction vessel. Otherwise there exists the possibility that some ring-opening polymerization might occur during the early stages of the hydrosilation reaction, with the concomitant adverse effects on viscosity control.

If it is desired that the non-phosphine-containing transition-metal complex and the modifying phosphine ligand be added sequentially to the reaction vessel, then it is preferred that the modifying ligand be added to Components (A), (B), or both, prior to the addition of the non-phosphine-containing transition-metal complex.

To practice the method and make the composition of the present invention, Components (A), (B) and (C) are brought together in a reaction vessel of suitable size for the size of the batch. Addition of the Components is preferably with mixing. A volatile solvent, preferably toluene, xylene or hexane, may also be added to the reaction mixture in order to facilitate the mixing process and dispersion of the Components.

The epoxysilicone composition of the invention is then prepared by reacting the mixture of Components (A), (B) and (C) at a temperature in the range of from about 25° C. to about 120° C., preferably from about 25° C. to about 110° C. and most preferably from about 50° C. to about 100° C. In one embodiment of the invention, the present composition is readily prepared by first mixing Components (A) and (B), either in a reaction vessel or otherwise. Component (C) is then preferably added as a mixture of non-phosphine-containing transition-metal complex and modifying phosphine ligand (i.e., a phosphine-modified transition-metal complex). It is also preferable that Component (C) be added to the reaction vessel with mixing.

In another embodiment of the invention, the present composition is prepared by mixing Component (A) or (B), or both, in a suitable reaction vessel, followed by the addition of the appropriate amount of phosphine ligand as defined for Compound (C) of the method of the invention, and thereafter adding the non-phosphine-containing transition-metal complex in the amount as required.

In another embodiment of the invention, any two of Components (A), (B) or (C) as defined above can be pre-mixed, and the third Component then added later to produce the composition of the invention by the present method.

In another embodiment of the invention, any two of Component (A), Component (B), the phosphine ligand or non-phosphine-containing transition-metal complex of Component (C), may be first mixed together. The additional components may then be added thereafter, either as a mixture or individually, and the reaction process of the invention then completed. Such mixtures in this and the previous embodiment exemplify that the Components of the invention may be premixed so as to provide what is in practicing the invention essentially a two-component system for making a curable epoxysilicone.

After the completion of the hydrosilation reaction the volatile solvent can be removed from the composition of the invention through evaporation, preferably at elevated temperature and reduced pressure.

The temperature of devolitization is between from about 50° C. to about 130° C., preferably between from about 50° C. and about 100° C. and most preferably between from about 80° C. to about 100° C. If a tertiary amine stabilizer is incorporated into the practice of the present invention, then the temperature of devolitization is between from about 100° C. to about 250° C., preferably between about 125° C. and about 225° C., and most preferably between from about 150° C. and 200° C.

The pressure of the stripping step is generally preferred to be below atmospheric, as such reduced pressure aids in the release of volatile molecules from the composition of the invention. Preferably the stripping step is at less than 25 torr and most preferably at less than 10 torr.

The stripping of volatile molecules, including unreacted volatile Components and low molecular weight side products of the hydrosilation reaction, may be conveniently achieved through use of a rotary evaporator, thin film evaporator, wiped film evaporator or the like.

The curable composition of the invention can be applied to cellulosic and other substrates including paper, metal, foil, polyethylene-coated Kraft paper (PEK), supercalendered Kraft paper, polyethylene films, polypropylene films and polyester films. In general, coatings can be applied to these substrates at the desired thickness. For example, the composition of the invention is readily applicable by doctor blade. For applications as a release coating, the composition of the invention is applied at a thickness of between about 0.1 mil and about 10 mils; it is also convenient to refer to such coatings in terms of coat weights, typically about 1 g/m².

The application and dispersion of the curable composition of the invention to a substrate may be facilitated if the composition is added as a solution or dispersion in a volatile liquid carrier in which the epoxysilicone composition is soluble. When the curable composition is a polydimethylsiloxane, preferable volatile liquid carriers include, for example, hexane, xylene or toluene. It should be recognized, however, that when the curable composition of the invention is a copolymer, terpolymer, etc., the volatile solvent must be chosen such that the polymer is soluble in the solvent, which may depend upon the particular physical and chemical properties of the polymer as recognized in the art. The amount of volatile liquid carrier incorporated into the composition should not exceed about 3% by weight as compared to the total weight of the curable composition, if the advantages of using a relatively solvent-free composition are desired.

Curing of the composition of the invention can be either thermally or, in the presence of the appropriate photocatalyst and possibly cure accelerator, through UV irradiation.

Polymerization by heat involves the simple step of heating the epoxysilicones to a temperature of about 120° C. or greater, which causes the oxirane ring to open and thereby react. Reference is made in this regard to Pleudemann and Fanger, "Epoxyorganosiloxanes", *Journal of the American Chemical Society*, Vol. 81, pp. 2632–2635, 1959.

Polymerization by UV radiation involves the use of a photocatalyst that, when irradiated with UV light, forms an acid that catalyzes the crosslinking of epoxysilicone monomers through the epoxide ring-opening reaction. Such reactions are disclosed, for example, in U.S. Pat. No. 4,279,717 (Eckberg) and U.S. Pat. No. 4,617,238. Preparation of photoinitiator salts useful for epoxysilicone polymerization are disclosed, for example, in Crivello and Lee, "Alkoxy-Substituted Diaryliodonium Salt Cationic Photoinitiators", *Journal of Polymer Science, Part A: Polymer Chemistry*, Vol. 27, John Wiley, New York 1989, pp. 3951–3968.

Cure performance of the composition of the invention and adhesion of the epoxysilicone product may be enhanced by the addition of epoxide monomers to the composition of the invention after the hydrosilation reaction is completed. For example, addition of up to 10 parts of an aliphatic epoxide monomer for every 10 parts epoxysilicone may result in composition exhibiting superior UV cured and anchorage on porous cellulose paper as compared to similar compositions without these "reactive diluents".

In order that persons skilled in the art may better understand the practice of the present invention, the following examples are provided by way of illustration, and not by way of limitation. Additional information which may be useful in state-of-the-art practice may be found in each of the references and patents cited herein, which are hereby incorporated by reference.

EXPERIMENTAL

Unless otherwise indicated, all resins and catalysts are available from General Electric Silicones, Waterford, New York. 1,1,3,3-tetramethyldisiloxane was purchased from Silar Laboratories. Phosphine ligands used herein were purchased as the pure compounds, available from the Aldrich Chemical Company. For Examples 19 and Comparative Example 19A, n-butylsilane was purchased from the Silar Chemical Company. ¹H NMR spectra were recorded on a Varian XL 200-MHz spectrometer, a Hewlett-Packard 5840A Gas Chromatograph was used for gas phase chromatographic analysis.

In the shorthand notation of polymer structure below, the following applies:

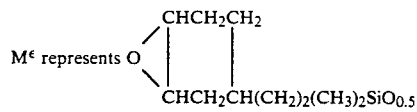

Additionally, the notation (metal catalyst/phosphine ligand) is used to indicate those systems in which a mixture of non-phosphene-containing transition-metal complex and modifying phosphine ligand was used as catalyst in the method of the invention. Unless stated otherwise, the phophine-modified transition-metal complexes of Component (C) in the Examples below were premixed prior to addition of the catalyst to Components (A) and (B).

EXAMPLE 1

To 1.0 gram of cyclohexene oxide was added 1.0 gram 1,1,3,3-tetramethyldisiloxane and approximately 5 mg Pt[(C₆H₅)₃P]₄. The mixture was brought to, and maintained for about 20 hours at a temperature of about 55° C. No reaction was observed to take place, indicating that this catalyst does not facilitate the epoxide ring-opening polymerization reaction.

COMPARATIVE EXAMPLE 1A

To 1.0 gram of cyclohexene oxide was added 1.0 gram 1,1,3,3-tetramethyldisiloxane and approximately 5 mg of $H_2PtCl_6$ in octanol ("Lamoreaux's catalyst"; 3.5% Pt) and the temperature was increased to about 100° C. A rapid, exothermic polymerization reaction took place immediately, indicating the this catalyst efficiently promotes the epoxide ring-opening polymerization reaction.

COMPARATIVE EXAMPLE 1B

The procedure of Example 1 was repeated with the exception that about 3 drops of an ethanol solution of the Ashby catalyst containing 1.75% Pt was used in place of the Lamoreaux catalyst. Again, a rapid exothermic epoxide ring-opening polymerization reaction was observed, indicating that this catalyst also efficiently promotes the polymerization of epoxides.

COMPARATIVE EXAMPLE 1C

The procedure of Example 1 was again followed with the exception that about 3 drops of the Karstedt catalyst containing 5% Pt (Karstedt catalyst) was used in place of the Lamoreaux catalyst. Again a rapid, exothermic polymerization reaction was observed.

EXAMPLE 2

The procedure described in Example 1 was repeated, with the exception that about 5 mg of $RhCl[(C_6H_5)_3P]_3$ catalyst was used in place of the platinum catalyst. As in Example 1, no reaction was observed, indicating that the tris(triphenylphosphine)rhodium chloride catalyst also does not promote the epoxide ring-opening polymerization reaction under the conditions similar to that of a hydrosilation addition reaction.

EXAMPLE 3

The procedure described in Example 1 was repeated with the exception that a mixture containing about 2 mg $[RhCl(cyclooctadiene)]_2$ and 4 mg of $(C_6H_5)_3P$ was used. No ring-opening polymerization reaction was observed.

COMPARATIVE EXAMPLE 3A

The procedure described in Example 3 was repeated with the exception that the catalyst was 2 mg $[RhCl(cyclooctadiene)]_2$ without the modifying triphenylphosphine ligand. A rapid exothermic reaction immediately took place, indicating that the $[RhCl(cyclooctadiene)]_2$ catalyst is non-selective for the hydrosilation reaction in the absence of the modifying phosphine ligand.

EXAMPLE 4

The procedure described in Example 1 was again repeated with the exception that the hydrosilation catalyst was 2 mg $[IrCl(cyclooctadiene)]_2$ modified with 4 mg triphenylphosphine as in Example 3. No polymerization reaction of the cyclohexene oxide was observed.

COMPARATIVE EXAMPLE 4A

The procedure of Example 4 was repeated with the exception that the catalyst was about 2 mg $[IrCl(cyclooctadiene]_2$ without the modifying triphenylphosphine ligand. A swift polymerization reaction was observed indicating that this catalyst also effectively promotes the epoxide ring-opening polymerization reaction under conditions similar to those of a hydrosilation addition reaction.

EXAMPLE 5

Again, the procedure of Example 1 was performed, except that the catalyst was a mixture of 2 mg $[IrCl(cyclooctadiene)]_2$ and 4 mg triphenylphosphine modifier. No reaction was observed, indicating that this modified catalyst does not promote the epoxide ring-opening reaction under these conditions.

COMPARATIVE EXAMPLE 5A

The procedure of Example 5 was repeated, save the catalyst was 2 mg unmodified $[IrCl(cyclooctadine)]_2$. As in the other above-mentioned Comparative Examples, the non-phosphine-containing catalyst promoted a rapid polymerization reaction of the cyclohexene oxide.

EXAMPLE 6

Into a 100 mL round bottom flask equipped with a magnetic stirrer and a reflux condenser were added 10.0 grams 4-vinylcyclohexene oxide (VCHO) and 5.6 grams 1,1,3,3-tetramethyldisiloxane. To this mixture was then added about 5 mg of tris(triphenylphosphine)rhodium chloride and 30 mL toluene. The mixture was brought to about 100° C. and maintained at this temperature for about 2 days, with stirring. The epoxysilicone product was isolated in quantitative yield by removing the solvent using a rotary evaporator. 1H NMR confirmed the structure of the product of the reaction to be the expected 1,2di(2-(4-cyclohexene oxide)ethyl)-1,1,3,3-tetramethyldisiloxane, $M^eM^e$. Gas phase chromatographic analysis demonstrated the absence of any higher molecular weight polymers in the hydrosilation reaction product, indicating that the tris(triphenylphosphine)rhodium chloride catalyst is highly selective for the hydrosilation reaction as compared to the epoxide ring-opening reaction.

EXAMPLE 7

Following the procedure of Example 6, 4.0 grams 4-vinylcyclohexene oxide, 2.0 grams 1,1,3,3-tetramethyldisiloxane, 15 mL toluene and 5 mg $Pt[(C_6H_5)_3P]_4$ were combined together and heated at between about 50° C. to 60° C. for about 20 hours. A quantitative yield of the expected $M^eM^e$ product was obtained.

EXAMPLE 8

The procedure and components as in Example 7 were used, with the exception that the catalyst was a mixture consisting of 2 mg $[RhCl(cyclooctadiene)]_2$ and 4 mg $(C_6H_5)_3P$. A rapid hydrosilation addition reaction took place giving identical results as obtained with the platinum triphenylphosphine catalyst in Example 7.

EXAMPLE 9

The procedure and components as set forth in Example 7 were used with the exception that the catalyst was a mixture consisting of $[IrCl(cyclooctadiene)]_2/(C_6H_5)_3P$ modifier as in Example 5. The selective hydrosilation as in Example 7 was obtained.

EXAMPLE 10

The procedure and components were as set forth in Example 7, with the exception that a catalyst consisting of $[RhCl(cyclooctadiene)]_2/(C_6H_5)_3P$ was generated in the reaction mix instead of using a premixed phosphine-modified transition-metal complex as catalyst. The in situ production of phosphine-modified catalyst was accomplished by the addition of 5 mg triphenylphosphine and 2 mg [RhCl(cyclooctadiene)]2 to the mix of 4-vinylcyclohexene oxide, 1,1,4,4-tetramethyldisiloxane and toluene. As in Example 7-9, a highly selective hydrosilation reaction was obtained. This Example indicated that the selective hydrosilation catalyst of the invention can be conveniently generated in situ.

EXAMPLE 11

The procedure and components as in Example 7 were used with the exception that the catalyst was about 5 mg of cis-Pt[$(C_6H_5)P]_2Cl_2$. A selective hydrosilation reaction was obtained with no evidence of an oxirane ring-opening polymerization of either the 4-vinylcyclohexene oxide starting material or the $M^{\epsilon}M_{\epsilon}$ product.

EXAMPLE 12

The procedure and components as in Example 7 were used with the exception that the catalyst was about 5 mg of trans-Pt[$(C_6H_5)_3P]_2Cl_2$. This phosphine-containing catalyst also efficiently promoted the hydrosilation reaction without any evidence promoting the oxirane ring-opening reaction.

EXAMPLE 13

The procedure and components as in Example 7 were used with the exception that the catalyst was about 5 mg of RhCl(CO)[$(C_6H_5)_3P]_2$. Only the selective hydrosilation reaction was detected.

EXAMPLE 14

The procedure and components as in Example 7 were used with the exception that the catalyst was about 5 mg of RhH(CO)[$(C_6H_5)_3P]_3$. This phosphine-containing catalyst also promoted only the hydrosilation reaction.

EXAMPLE 15

The procedure and components as in Example 8 were used to generate an $M^{\epsilon}M^{\epsilon}$ epoxysilicone with the exception that 3 mg of $(C_6H_5)_2PCHCHP(C_6H_5)_2$ was used as catalyst modifier in place of the triphenylphosphine modifier. Again, only the selective hydrosilation reaction was detected. The results of this reaction exemplify that the phosphine ligand in the catalyst of the invention need not be in the form of triphenylphosphine.

EXAMPLE 16

The procedure and components as in Example 8 were used to generate an $M^{\epsilon}M^{\epsilon}$ epoxysilicone with the exception that 3 mg of $(C_6H_5)_2PCH_2CH_2P(C_6H_5)_2$ was used as catalyst modifier in place of the triphenylphosphine modifier. Only the selective hydrosilation reaction was detected. This reaction.

EXAMPLE 17

The procedure and components as in Example 8 were used to generate an $M^{\epsilon}M^{\epsilon}$ epoxysilicone with the exception that 3 mg of $(CH_3CH_2)_2PCH_2CH_2P(CH_2CH_3)_2$ was used as catalyst modifier in place of the triphenylphosphine modifier. Only the selective hydrosilation reaction was again detected.

EXAMPLE 18

The procedure and components as in Example 8 were used to generate an $M^{\epsilon}M^{\epsilon}$ epoxysilicone with the exception that 3 mg of tri-n-butylphosphine was used as catalyst modifier in place of the triphenylphosphine modifier. Again only the hydrosilation reaction was detected.

The above Examples are illustrative that the phosphine-containing and phosphine-modified catalysts of the invention are highly effective at promoting the hydrosilation addition reaction between an ethylenically unsaturated epoxide and an SiH-containing silicon compound, without promoting the oxirane ring-opening reaction of the epoxide starting material or the epoxysilicone product.

EXAMPLE 19

A convenient procedure for determining whether a particular hydrosilation catalyst effectively promotes a epoxide ring-opening polymerization reaction is to determine if the catalyst promotes polymerization of a saturated epoxide in the presence of n-butylsilane and under reaction conditions similar to that of a hydrosilation reaction. Such a test scheme is advantageous in that all polymerization is expected to be limited to the ring-opening type since there is no unsaturation present in the epoxide, and therefore the primary reaction products can be predicted with a substantial degree of certainty. Thus, analysis of the reaction products is not hampered by competing hydrosilation reactions or unpredictable side products. An example of such a test procedure is when 2 mg of the hydrosilation catalyst [RhCl(cyclooctadiene)]2 is contacted with 2 grams cyclohexene oxide in the presence of 20 mg n-butylsilane at room temperature. A rapid, exothermic polymerization reaction occurs with the formation of linear poly(cyclohexene oxide). Such results allow one to conclude that the particular catalyst does promote oxirane ring-opening polymerization. These conclusions are confirmed by $^1$H NMR and gas phase chromatography.

COMPARATIVE EXAMPLE 19A

The procedure in Example 19 was repeated with the exception that 3 mg of triphenylphosphine was added to the rhodium catalyst prior to the addition of catalyst to the n-butylsilane/cyclohexene oxide mixture. No reaction was observed with the triphenylphosphine present.

In order to test other hydrosilation catalysts for their ability to promote oxirane ring-opening polymerization in the method of the invention, one need only replace the [RhCl(cyclooctadiene)]2 in Example 19 above with an amount of the test catalyst that is effective in promoting the hydrosilation reaction. One may then also determine whether phosphine modification eliminates the promotion of the oxirane ring-opening reaction by incorporating, for example, triphenylphosphine in the reaction mixture as exemplified in the Examples and concentration ranges contained herein. Additionally, using the procedure set forth in Comparative Example 19A, one may easily determine the minimum effective weight ratio of phosphine ligand to transition-metal catalyst required to impart hydrosilation specificity on that transition-metal hydrosilation catalyst.

It is understood that various other modifications will be apparent to and can be readily made by those skilled in the art without departing from the scope and spirit of the present invention. Accordingly, it is not intended that the scope of the claims appended hereto be limited to the description set forth above but rather that the claims be construed as encompassing all of the features of patentable novelty which reside in the present invention, including all features which would be treated as equivalents thereof by those skilled in the art to which the invention pertains.

What is claimed is:

1. A method for making an epoxysilicone composition comprising the steps of:
   (i) preparing a mixture comprising:
   (A) 1 part by weight of an ethylenically unsaturated epoxide;
   (B) from about 0.5 to about 400 parts by weight of an organohydrogensiloxane or an organohydrogensilane, as compared to the weight of (A); and
   (C) from about 1 to about 5000 parts per million by weight as compared to the weight of (A) a hydrosilation catalyst comprising a phosphine ligand and a non-phosphine-containing transition-metal complex; and wherein the weight ratio of said phosphine ligand to said non-phosphine-containing transition-metal complex in said mixture is from about 1:10 to about 250:1.
   (ii) reacting the mixture of said step (i) under conditions which promote a hydrosilation addition reaction between an olefin epoxide and a silicon hydride to produce an epoxysilicone product, and which do not promote an epoxide ring-opening reaction in either (A) or in said epoxysilicone product.

2. The method as set forth in claim 1, wherein in step (i) said non-phosphine-containing transition-metal complex is a platinum, palladium, rhodium, iridium, iron or cobalt complex.

3. The method as set forth in claim 2, wherein in step (i) said non-phosphine-containing transition-metal complex is selected from the group consisting of:
$RhX_3(SR_2)_3$; $RhX_3.xH_2O$; $[RhX(norbornadiene)]_2$; $[RhCl(cyclooctadiene)]_2$; $[RhCl(C_2H_4)_2]_2$; $[RhCl(CO)_2]_2$; $[Rh(CO)_2(C_5H_7O_2)]$; $Rh_2(CH_3CO_2)_4$; $[Rh(C_7H_{15}O_2)_2]_2$; $Rh(C_2H_8N_2)_3Cl_3.3H_2O$; $Rh(C_5H_7O_2)_3$; $[IrCl(cyclooctadiene)]_2$; $[IrCl(CO)_3]n$; $Ir(CO)_2(C_5H_7O_2)_2$; $cis-[Ir(C_2H_8N_2)_2Cl_2]Cl$; $H_2IrCl_6.xH_2O$; $IrCl_3.H_2O$; $Pt(pyridine)_2Cl_2$; $H_2PtCl_6.xH_2O$; $(NH_4)_2PtCl_6.xH_2O$; $H_2PtBr_6.xH_2O$; $PtCl_2(cyclooctadiene)$; $PtBr_2(cyclooctadiene)$; $PtI_2(cyclooctadiene)$; $[PtCl(C_2H_4)_2]_2$;$cisPt[(CH_3CH_2)_2S]_2Cl_2$; $Pd(pyridine)_2Cl_2$; $[PdCl(C_3H_5)]_2$;$Pd(pyridine)_2(CH_3CO_2)_2$; $PdCl_2(cyclooctadiene)$; $PdCl_2(C_6H_5CN)_2$; $Pd(CH_3CO_2)_2$;and $Co_2(CO)_8$,
where X represents a halogen atom, x is 3 or 4 and n is an integer from about 2 to about 10.

4. The method as set forth in claim 1, wherein in step (i) said phosphine ligand is of the formula $PR_3^2$ wherein the $R^2$ groups are individually substituted or unsubstituted $C_{1-8}$ aryl, arylalkyl, or alkaryl radicals.

5. The method as set forth in claim 4, wherein in step (i) said phosphine ligand is selected from the group consisting of triphenylphosphine, triethylphosphine, tri-n-butylphosphine, trimethylphosphine, diphenylmethylphosphine and dimethylphenylphosphine.

6. The method as set forth in claim 1, wherein in step (i), said ethylenically unsaturated epoxide is selected from the group consisting of allyl glycidyl ether; methallyl glycidyl ether; 1-methyl-4-isopropenyl cyclohexene oxide; 2,6-dimethyl-2,3-epoxy-7-octene; 1,4-dimethyl-4-vinylcyclohexene oxide; 4-vinylcyclohexene oxide; vinylnorbornene monoxide; dicyclopentadiene monoxide; 1,2-epoxy-6-heptene; and 1,2-epoxy-3-butene.

7. The method as set forth in claim 1, wherein in step (i) said organohydrogensiloxane is a polydimethyl siloxane-polymethylhydrogen siloxane copolymer.

8. The method as set forth in claim 1, wherein in step (i) said phosphine ligand and said non-phosphine-containing transition-metal complex of (C) are mixed together prior to addition of said hydrosilation catalyst to (A) or (B).

9. The method as set forth in claim 1, wherein in step (i) said phosphine ligand of (C) is mixed with (A) or (B) prior to the addition of said non-phosphine-containing transition-metal complex to said mixture.

10. The method as set forth in claim 1, wherein in step (i) said non-phosphine-containing transition-metal complex in (C) is mixed with (A) and (B) prior to the addition of said phosphine ligand in (C) to said mixture.

11. A curable composition comprising an epoxysilicone, a non-phosphine-containing transition-metal complex and a phosphine ligand.

12. The curable composition set forth in claim 11, wherein said non-phosphine-containing transition-metal complex is a platinum, palladium, rhodium, iridium, iron or cobalt complex.

13. The curable composition set forth in claim 12, wherein said non-phosphine-containing transition-metal complex is selected from the group consisting of:
$RhX_3(SR_2)_3$;$RhX_3.xH_2O$; $[RhX(norbornadiene)]_2$; $[RhCl(cyclooctadiene)]_2$;$[RhCl(C_2H_4)_2]_2$; $[RhCl(CO)_2]_2$;$[Rh(CO)_2(C_5H_7O_2)]$; $Rh_2(CH_3CO_2)_4$; $[Rh(C_7H_{15}O_2)_2]_2$;$Rh(C_2H_8N_2)_3Cl_3.3H_2O$; $Rh(C_5H_7O_2)_3$; $[IrCl(cyclooctadiene)]_2$;$[IrCl(CO)_3]n$; $Ir(CO)_2(C_5H_7O_2)_2$;$cis-[Ir(C_2H_8N_2)_2Cl_2]Cl$; $H_2IrCl_6.xH_2O$; $IrCl_3.H_2O$; $Pt(pyridine)_2Cl_2$; $H_2PtCl_6.xH_2O$; $(NH_4)_2PtCl_{16}.xH_2O$; $H_2PtBr_6.xH_2O$; $PtCl_2(cyclooctadiene)$; $PtBr_2(cyclooctadiene)$; $PtI_2(cyclooctadiene)$; $[PtCl(C_2H_4)_2]_2$;$cisPt[(CH_3CH_2)_2S]_2Cl_2$; $Pd(pyridine)_2Cl_2$; $[PdCl(C_3H_5)]_2$;$Pd(pyridine)_2(CH_3CO_2)_2$; $PdCl_2(cyclooctadiene)$; $PdCl_2(C_6H_5CN)_2$; $Pd(CH_3CO_2)_2$;and $Co_2(CO)_8$,
where X represents a halogen atom, x is 3 or 4 and n is an integer from about 2 to about 10.

14. The curable composition set forth in claim 11, wherein said phosphine ligand is of the formula $PR_3^2$ wherein the $R^2$ groups are, individually, substituted or unsubstituted $C_{1-8}$ alkyl or aryl, arylalkyl, or alkaryl radicals.

15. A method of preventing oxirane-ring opening during a hydrosilation reaction between an ethylenically unsaturated epoxide and a organohydrogensilane or organohydrogensiloxane comprising the steps of:
   (i) preparing a mixture comprising:
   (A) 1 part by weight of an ethylenically unsaturated epoxide;
   (B) from about 0.5 to about 400 parts by weight of an organohydrogensilane or organohydrogensiloxane, as compared to the weight of (A);
   (C) from about 1 part to about 5000 parts per million of a phosphine-containing transition-metal complex or phosphine-modified transition-metal complex hydrosilation catalyst; and
   (ii) reacting the mixture of said step (i) under conditions which promote a hydrosilation addition reaction between an olefin epoxide and a silicon hydride to produce an epoxysilicone product, and which do not promote an epoxide ring-opening reaction in either (A) or in said epoxysilicone product.

* * * * *